United States Patent [19]

Hartert

[11] 4,312,217

[45] Jan. 26, 1982

[54] APPARATUS AND METHOD FOR MEASURING CHANGES IN CONDITIONS IN COAGULATING LIQUIDS

[75] Inventor: Hellmut Hartert, Kaiserslautern, Fed. Rep. of Germany

[73] Assignee: Dr. E. Fresenius Chem.-pharm Industrie KG, Oberursel, Fed. Rep. of Germany

[21] Appl. No.: 133,649

[22] Filed: Mar. 21, 1980

Related U.S. Application Data

[63] Continuation of Ser. No. 941,587, Sep. 12, 1978, Pat. No. 4,202,204.

[30] Foreign Application Priority Data

Sep. 13, 1977 [DE] Fed. Rep. of Germany ....... 2741060

[51] Int. Cl.³ ..................... G01N 11/10; G01N 33/48
[52] U.S. Cl. .......................................... 73/64.1; 73/59
[58] Field of Search ....................... 73/64.1, 59, 60, 54

[56] References Cited

U.S. PATENT DOCUMENTS

| | | |
|---|---|---|
| 3,225,588 | 12/1965 | Moulin et al. . |
| 3,349,604 | 10/1967 | Banks . |
| 3,382,706 | 5/1968 | Fitzgerald . |
| 3,587,295 | 6/1971 | Simons . |
| 3,714,815 | 2/1973 | Hartert ................................ 73/64.1 |
| 3,722,262 | 3/1973 | Gilison, Jr. et al. ..................... 73/59 |
| 3,751,975 | 8/1973 | Katsura .................................... 73/59 |
| 3,943,753 | 3/1976 | Simon . |
| 4,026,671 | 5/1977 | Simons et al. . |
| 4,045,999 | 9/1977 | Palmer .................................... 73/59 |
| 4,148,216 | 4/1979 | Do et al. .................................. 73/59 |
| 4,154,093 | 5/1979 | Smith et al. . |
| 4,193,293 | 3/1980 | Cavallari ............................... 73/64.1 |

FOREIGN PATENT DOCUMENTS

| | | |
|---|---|---|
| 2741060 | of 0000 | Fed. Rep. of Germany . |
| 847076 | 8/1952 | Fed. Rep. of Germany . |
| 1558516 | 1/1969 | France .................................. 73/64.1 |
| 2004376 | of 0000 | United Kingdom . |
| 851621 | 10/1960 | United Kingdom . |
| 1233881 | 6/1971 | United Kingdom . |
| 507805 | 4/1976 | U.S.S.R. ............................... 73/64.1 |
| 602825 | 4/1978 | U.S.S.R. ............................... 73/64.1 |

OTHER PUBLICATIONS

"Piezoelectric Method of Determining Viscosity at 40 KHZ", W. H. Robinson et al., pp. 1070–1076, Mar. 1978, Journal of Applied Physics, vol. 49, No. 3.

*Primary Examiner*—Charles A. Ruehl
*Assistant Examiner*—Joseph W. Roskos
*Attorney, Agent, or Firm*—Cushman, Darby & Cushman

[57] ABSTRACT

The coagulation of blood is measured by introducing the blood into an annular gap in a beaker formed between the inner surface of the beaker and a cylindrical member depending into the beaker. The beaker is mounted on the upper end of a rod-like support. A coil arrangement about the lower part of the rod-like support impresses a circular orbiting motion on the support and beaker. Another core associated with the rod-like support measures changes in amplitude of the support produced by the development of fibrin in the blood sample in the annular gap.

18 Claims, 2 Drawing Figures

FIG. 1
FIG. 2
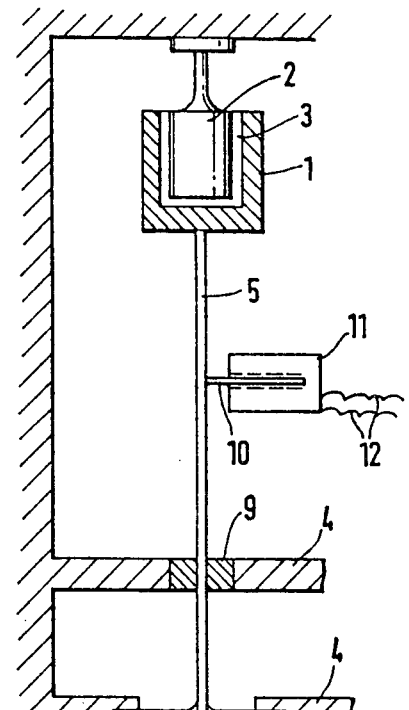
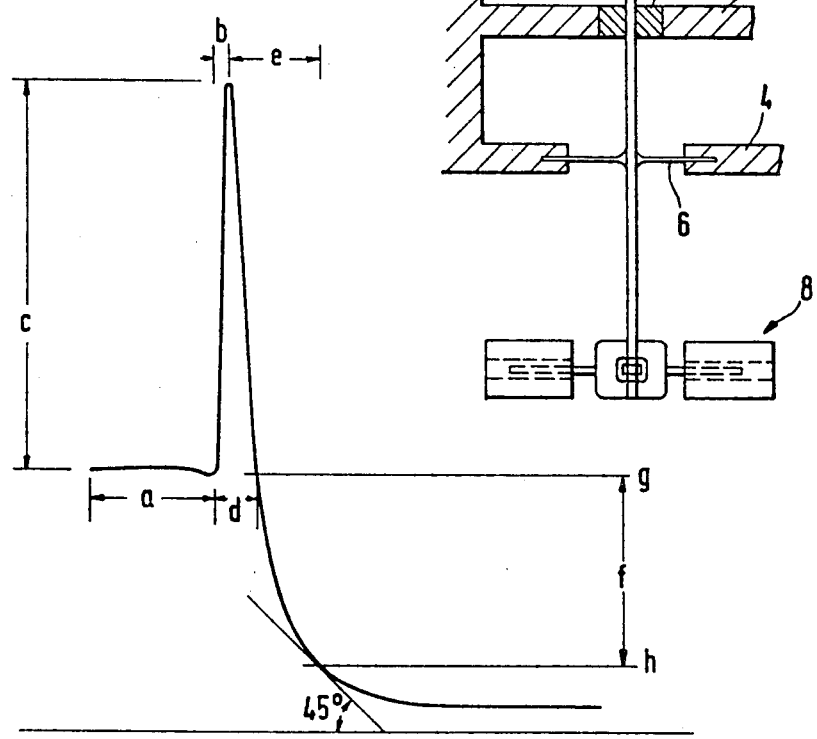

APPARATUS AND METHOD FOR MEASURING CHANGES IN CONDITIONS IN COAGULATING LIQUIDS

This application is a continuation of my copending application Ser. No. 941,587, filed Sept. 12, 1978, now U.S. Pat. No. 4,202,204 issued May 13, 1980, based on a referenced priority document, which are incorporated hereinto by reference.

BACKGROUND OF THE INVENTION

Applicant's own earlier U.S. Pat. No. 3,714,815 relates to an apparatus for performing continuous measurements of coagulating liquids, preferably blood and derivatives thereof. The apparatus has means for producing shearing and deformation effects in the coagulating fluid, which means are in the form of a circularly cylindrical beaker and a test member which is also of circularly cylindrical configuration and is suspended from a torsion wire and is located in the beaker. An annular gap for receiving the fluid is formed between the beaker and the test member. An orbital motion is imparted by appropriate means to the wall surfaces of the beaker which confine the fluid.

This apparatus is designed and adjusted such that the peripheral speed of the orbital movement substantially approximates the rate of flow of the blood in human blood vessels. In this patent, it has already also been proposed, inter alia, to produce the orbital movement by a rotating electrical field which correspondingly acts upon the beaker.

Thus, it has been known to measure the coagulation of blood by subjecting the fibrin, produced during coagulation, to a specific shearing stress. By appropriate metering of this shearing stress, the resilient resistance of the coagulum can be increased far more rapidly compared with an apparatus in which the fulid is not subjected to a metered shearing stress of this kind during coagulation, that is, during the formation of the coagulum. Thus, it is far simpler to distinguish between normal and pathological blood coagula than with the original apparatus described in the inventor's U.S. Pat. No. 3,714,915. This renders it possible to provide a substantial improvement in the diagnostic routine. At the same time, it is possible to afford a sharp definition of the so-called coagulation time which elapses until the coagulum commences to form and which is normally difficult to define.

SUMMARY OF THE INVENTION

Based on the fundamental ideas of the that patent, and in accordance with the invention, an improved apparatus is proposed as well as a preferred measuring method to be performed by this improved apparatus.

The improved apparatus is distinguished essentially in that the beaker for receiving the fluid is arranged at the upper end of an upright resilient rod. Located around the lower end of the rod a plurality of coils forming a rotating electro-magnetic field. Cores entering the coils are secured to and extend radially from the rod. The movemet of the entire arrangement, produced by the various components of the measuring apparatus and the fluid to be measured, is picked up by a further, laterally disposed coil whose core is also arranged radially on the rod. The rod is clamped in a resilient diaphragm which extends radially from the rod and serves to hold the entire arrangement.

Furthermore, a vibration-damping element acting upon the rod may be provided.

In the first instance, the same measurements with the evaluation of the same changes in the fluid to be measured can be performed by this arrangement as are performed by the apparatus disclosed in U.S. Pat. No. 3,714,815. However, in addition to this, the present arrangement can be adjusted in a simple manner to a specific natural oscillation frequency, this being of importance in connection with the method to be performed by the present apparatus.

With this method, the measured values are ascertained in the resonance range of the natural oscillation of the measuring arrangement. Unexpectedly, it has transpired that, with a method of this type, the values coming from the pick-up coil and which can be recorded by, for example, a curve tracer, exhibit distinct maxima in dependence upon the states of change which are of interest in the fulid to be measured.

Furthermore, it was found that the most favourable natural frequency of the arrangement is approximately 35 Hz, and usable measurement results can also be obtained at approximately twice the frequency and half the freuency, only, of course, taking into account certain variations in wave length and wave amplitude which are dependent upon one another, i.e. the frequency and the amplitude.

Thus, the formation of the resilient fibrin coagulum can be detected with even greater sensitivity by the new apparatus in that the resilient resistance of the fibrin coagulum, increasing during coagulation, leads to the change of the natural frequency of the resiliently suspended measuring sensor, that is, the rod. This rod be be regarded as an orbitally oscillating pendulum. This change in the natural frequency leads to a shift relative to the forced drive frequency. According to the chosen starting position, there is a phase shift between the measuring sensor and the drive and also a change in amplitude in strict dependence, hitherto not attained, upon the quality and the quantity of the formation of the resilient material, such as the fibrin coagulum in the blood, which are thus rendered measurable.

The shearing stress exerted in a physiologically limited range on the coagulum produced, multiplies the resilient resistance of the fibrin network if the mechanical load resulting from the shearing stress acts during the production of the fibrin network. In other words, the fibrin network would be substantially more open in the final state if it were not built up under shearing load. Furthermore, the resonance shift caused by be object to be measured, that is the fibrin coagulum, is rendered usable for the measurement. Both of these factors lead to a considerable increase in, and thus easier recognition of, the differences between normal and pathological coagulation processes.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWING

FIG. 1 is an elevational view partly in section of a measuring apparatus embodying the present invention; and FIG. 2 is a graphic representation of the measurements made with the apparatus in FIG. 1.

DETAILED DESCRIPTION OF THE INVENTION

FIG. 1 shows the parts which are important and critical to the action of the apparatus. A cylindrical member 2 is inserted in a known manner into a beaker 1 which is at the same time the actual testing member. The fluid, whose coagulation processes are to be measured, is introduced into the annular gap 3 formed between the two parts. In contrast to the rheosimulator, the cylindrical member 2 is rigidly connected to the frame 4 of the apparatus. The beaker 1 is arranged at the upper end of a rod 5 which is made from rigid material and which is mounted in the frame 4 of the apparatus by means of a circular resilient diaphragm 6. A coil arrangement 8 at the lower end of the rod 5 produces a rotating electro-magnet field and imparts to the rod 5 an orbital movement which differs in a specific manner from the natural frequency of the rod 5 and which is of, for example, somewhat higher frequency. The circular oscillation can be damped by means of a damping device 9. The damping device can comprise, for example, an annular member of resilient or non-resilient material which is mounted in the frame 4 and which embraces the rod 5.

A further core 10, which enters a pick-up coil 11, is arranged on and extends radially of the rod 5 and is connected by way of leads 12 to any optional indicating element such as a curve tracer.

The curve which is shown in FIG. 2 and which is plotted by, for example, a curve tracer of this type, clearly shows the maximum indicating the state of change. It is caused by the fact that the resilient fibrin produced in the annular gap increases the natural frequency of the orbital movement of the rod and thus shifts the orbital movement of the rod into the range of the forced frequency. The resonance occurring thereby causes the increase in amplitude, i.e. the maximum of the curve. This is exceeded and leads to the reversal of the curve as soon as the resilient moment of the coagulum increases the natural frequency of the apparatus beyond the forced frequency. Thus, very slight changes in the state of the coagulum produced, in which, for example, the blood-platelets are also involved, are manifested in a pronounced manner by the characteristic and shape of the measured curve.

The measurement curve ("resonance thrombograph") shows the following features which are given as measured variables in minutes and seconds in the horizontal and in mm in the perpendicular:

(a) = coagulation time
(b) = curve rise time
(c) = maximum amplitude
(d) = short curve descent time
(e) = long curve descent time
(f) = negative amplitude
(g) = base line ("starting deflection")
(h) = zero line (zero amplitude)

Measurement of the values of a, c and d or e is sufficient for the routine assessment of the measurement curve.

Patent claims:

1. A method for measuring the changes of state in solidifying fluids particularly the changes occurring in the coagulation of blood, comprising the steps of:
mounting a measuring vessel on a support in a measuring system,
introducing a fluid into the measuring vessel,
impressing a constant excitation frequency on the support to stimulate the support into a forced oscillatory movement at a frequency at least near the natural frequency of the measuring system, and
measuring the amplitude of the support for determining the change in state of the solidifying fluid,
said constant excitation frequency corresponding at at least one time during the measuring to the changing resonant frequency of the measuring system.

2. The method of claim 1 including the step of selecting the excitation frequency higher than the natural frequency of the support where the fluid being measured is blood.

3. The method of claim 1 or 2 wherein the natural frequency of the support is in the range of 17 and 70 Hz.

4. The method of claim 3 wherein the natural frequency is 35 Hz.

5. Apparatus for measuring change of state in solidifying fluids, comprising:
a beaker,
an oscillatory driven means for mounting said beaker, and
a member inserted into said beaker,
wherein the improvement comprises:
said oscillatory driven means including an elastic support,
said beaker being mounted on said elastic support,
means including a coil arrangement for stimulating said elastic support into oscillation with a constant excitation frequency at least near the natural frequency of said elastic support so that oscillatory movement of said elastic support is produced, and
means for measuring the oscillatory amplitude of said elastic support,
said constant excitation frequency corresponding at at least one time during the measuring time to the changing resonant frequency of the oscillation.

6. Apparatus for measuring change of state in solidifying fluids, comprising:
vessel means for containing a said fluid,
means inserted into said vessel means for contacting fluid therein,
means for mounting one of said means stationary relative to the other said means, and
an oscillatory driven means for mounting said other means,
wherein the improvement comprises:
said oscillatory driven means including an elastic support,
said other means being mounted on said elastic support,
means including a coil arrangement for stimulating said elastic support into oscillation with a constant excitaton frequency at least near the natural frequency of said elastic support so that oscillatory movement of said elastic support is produced, and
means for measuring the oscillatory amplitude of said elastic support,
said constant excitation frequency corresponding at at least one time during the measuring time to the changing resonant frequency of the oscillation.

7. Apparatus as in claim 5 or 6 wherein said elastic support comprises a vertically extending resilient rod-like member.

8. Apparatus as in claim 5 or 6 wherein said coil arrangement comprises a coil generating an electromagnetic alternating field.

9. Apparatus as in claim 8 wherein the electromagnetic alternating field of said coil arrangement revolves in the circumferential direction of said rod-like member to cause the movement of said support to be orbital.

10. Apparatus as in claim 9 wherein said means for measuring the oscillatory amplitude comprises an oscillation sensor arranged for measuring the amplitude of the orbital movement of said elastic support without contact with said elastic support.

11. Apparatus as in claim 10 wherein said oscillation sensor is a rigidly mounted electromagnetic coil, and a movable core attached to and extending radially from said elastic support into said coil for measuring the amplitude of said elastic support.

12. Apparatus as in claim 11 including an indicating instrument connected to said electromagnetic coil for providing a trace of the change in amplitude of said elastic support.

13. A method for determining or monitoring data produced by changes of state in solidifying fluids, particularly changes occurring in the coagulation of blood, there being used in said method a resilient or an elastic oscillating system as sensing means, said method comprising the steps of:

influencing said system by fluid, exciting said system to perform oscillations at a rate at least in the proximity of its resonant frequency, said excitation of oscillating movement being performed by an impressed, constant excitation frequency which in the duration of the measurement at at least one time corresponds to the changing resonant frequency of said oscillating system, and continuously monitoring the amplitude of the oscillating movement.

14. In a method for the determination of measuring values produced by changes in the state of solidifying fluids, especially by the cogulation of blood, with an elastic oscillation system, acted upon by the fluid, as a detecting element, which is stimulated into oscillation at least near its natural frequency, the improvement characterized in that the oscillation stimulation is accomplished with a constant, superposed stimulation frequency, which, during the time of measurement corresponds at least at one time to the changing Eigen-frequency of the oscillation system.

15. A method for measuring the changes of state in solidifying fluids, particularly the changes occuring in the coagulation of blood, contained in measuring vessel means having insert means, comprising the steps of:

mounting one of said means stationary relative to the other said means, mounting said other means on a support in a measuring system, introducing a fluid into the measuring vessel means, impressing a constant excitation frequency on the support to stimulate the support into a forced oscillatory movement at a frequency at least near the natural frequency of the measuring system, and measuring the amplitude of the support for determining the change in state of the solidifying fluid, said constant excitation frequency corresponding at at least one time during the measuring to the changing resonant frequency of the measuring system.

16. The method of claim 15 including the step of selecting the excitation frequency higher than the natural frequency of the support where the fluid being measured is blood.

17. The method of claim 15 or 16 wherein the natural frequency of the support is in the range of 17 and 70 Hz.

18. The method of claim 17 wherein the natural frequency is 35 Hz.

* * * * *